United States Patent
Ogawa et al.

(10) Patent No.: US 8,301,402 B2
(45) Date of Patent: Oct. 30, 2012

(54) IN-PLANE COMPRESSIVE STRENGTH EVALUATION DEVICE AND METHOD THEREFOR

(75) Inventors: Naoki Ogawa, Hyogo (JP); Kengo Shimamura, Hyogo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/146,677

(22) PCT Filed: Dec. 18, 2009

(86) PCT No.: PCT/JP2009/071149
§ 371 (c)(1),
(2), (4) Date: Jul. 28, 2011

(87) PCT Pub. No.: WO2010/143324
PCT Pub. Date: Dec. 16, 2010

(65) Prior Publication Data
US 2011/0277554 A1 Nov. 17, 2011

(30) Foreign Application Priority Data
Jun. 10, 2009 (JP) .................................. 2009-139463

(51) Int. Cl.
*G01L 1/00* (2006.01)
*G01L 5/00* (2006.01)
*G05B 13/02* (2006.01)

(52) U.S. Cl. ................ 702/42; 702/33; 702/35; 702/41; 700/29; 700/30; 700/31

(58) Field of Classification Search .............. 702/33–35, 702/41–42; 700/29–31; 73/818
See application file for complete search history.

(56) References Cited

U.S. PATENT DOCUMENTS 5,779,442 A * 7/1998 Sexton et al. .............. 415/173.2
(Continued)

FOREIGN PATENT DOCUMENTS

CA 2677871 A1 10/2008
(Continued)

OTHER PUBLICATIONS

International Search Report for PCT/JP2009/071149, mailing date of Feb. 16, 2010.

*Primary Examiner* — Lisa Caputo
*Assistant Examiner* — Jonathan Dunlap
(74) *Attorney, Agent, or Firm* — Westerman, Hattori, Daniels & Adrian, LLP (57) ABSTRACT

An in-plane compressive strength evaluation device (10) provided with a memory unit (21) into which, when an in-plane compressive strength evaluation is actually performed using a test piece, an evaluation result is stored as first information; a first analysis unit (22) that obtains second information that is an evaluation result related to the load and a displacement of the structural model; an adjustment unit (23) that adjusts an elemental factor of the structural model that influences the in-plane compressive strength such that the second information approaches the first information; and a second analysis unit (24) that, in a state where the elemental factor used when the second information approaches the first information most closely expands the structural model into the structural form of the actual tube support plate, and that performs the in-plane compressive strength evaluation using the expanded structural model.

3 Claims, 9 Drawing Sheets

U.S. PATENT DOCUMENTS

| | | | |
|---|---|---|---|
| 5,832,421 A * | 11/1998 | Santoso et al. | 702/130 |
| 6,775,645 B2 * | 8/2004 | Daw et al. | 702/188 |
| 6,853,945 B2 * | 2/2005 | Namburi | 702/130 |
| 7,043,409 B1 * | 5/2006 | Schaffler et al. | 703/2 |
| 7,231,323 B2 * | 6/2007 | Weinberg et al. | 702/188 |
| 7,260,512 B2 * | 8/2007 | Mahe et al. | 703/2 |
| 7,353,140 B2 * | 4/2008 | Daw et al. | 702/182 |
| 7,493,237 B2 * | 2/2009 | Weinberg et al. | 702/188 |
| 8,065,022 B2 * | 11/2011 | Minto et al. | 700/29 |
| 2004/0204900 A1 * | 10/2004 | Namburi | 702/136 |
| 2009/0043406 A1 * | 2/2009 | Gauder et al. | 700/30 |
| 2010/0018687 A1 | 1/2010 | Muroya et al. | |
| 2011/0030866 A1 * | 2/2011 | Fadel et al. | 152/311 |
| 2011/0066258 A1 * | 3/2011 | Torzhkov et al. | 700/29 |

FOREIGN PATENT DOCUMENTS

| | | |
|---|---|---|
| EP | 2123977 A1 | 11/2009 |
| JP | 03-255892 A | 11/1991 |
| JP | 2772275 B2 | 7/1998 |
| JP | 2005-190073 A | 7/2005 |
| JP | 2006-258588 A | 9/2006 |
| JP | 2006-285381 A | 10/2006 |
| JP | 2008-102041 A | 5/2008 |
| JP | 2008-209063 A | 9/2008 |
| WO | 2008/120487 A1 | 10/2008 |

* cited by examiner

FIG. 11

IN-PLANE COMPRESSIVE STRENGTH EVALUATION DEVICE AND METHOD THEREFOR

TECHNICAL FIELD

The present invention relates to an in-plane compressive strength evaluation device that analyzes in-plane compressive strength of a tube support plate that is used in a steam generator, and to a method therefor.

BACKGROUND ART

In a nuclear power plant, primary cooling water that has been heated in a nuclear reactor is fed to a steam generator, secondary cooling water is heated in the steam generator with the heat of the primary cooling water to generate secondary steam, and the secondary steam is supplied to a steam turbine to rotate the steam turbine, thereby driving an electric generator.

Figure 9:
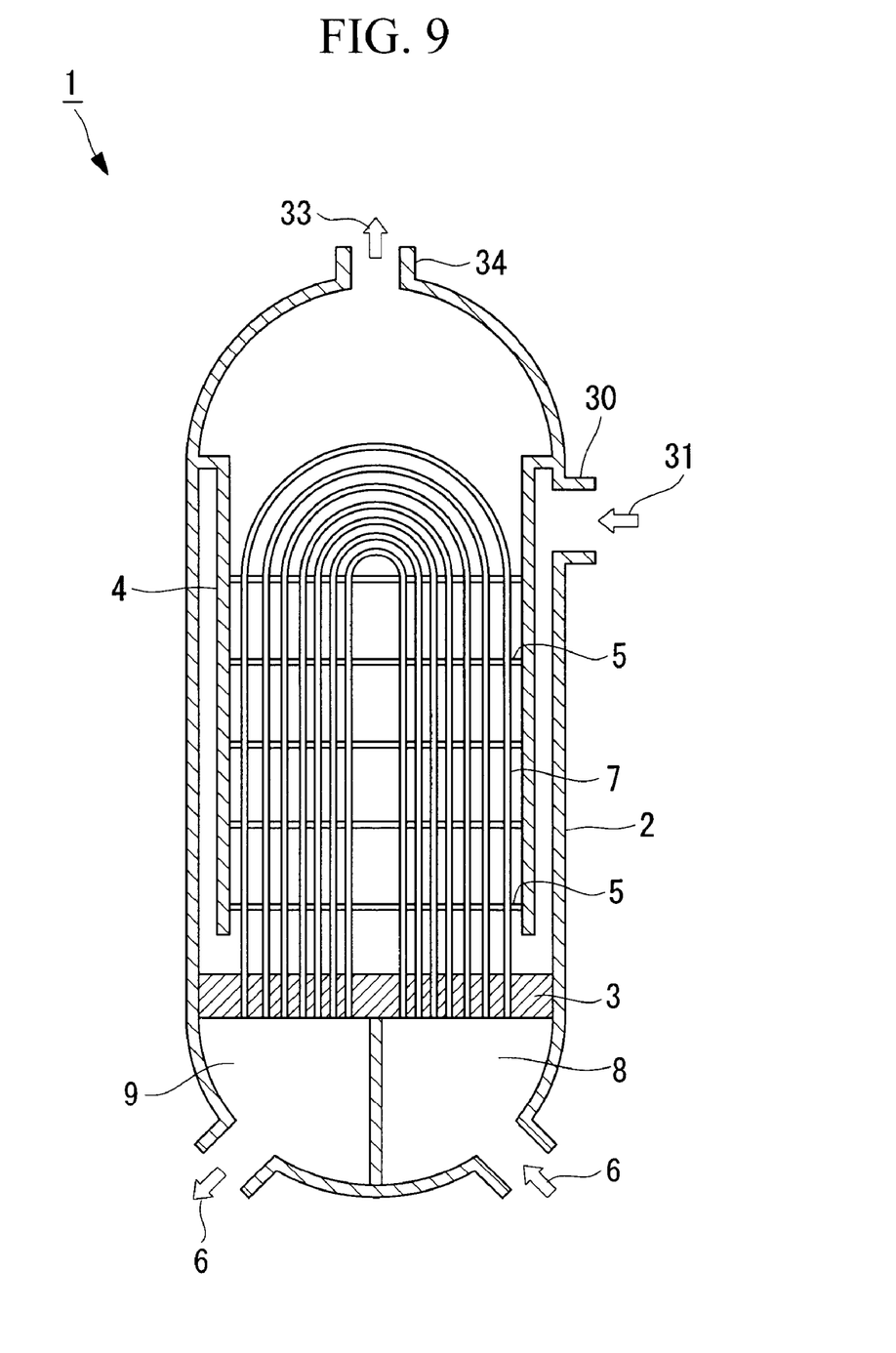
FIG. 9 is a diagram showing, in outline, the configuration of a steam generator used in a nuclear power plant.

FIG. 9 is a diagram showing, in outline, the configuration of a steam generator that is used in a nuclear power plant. As shown in FIG. 9, a steam generator 1 is provided with a solid outer cylinder 2, a tube plate 3 that is formed integrally with the outer cylinder 2, and a number of inverted U-shaped heat transfer tubes 7 both ends of which are inserted in and connected to the tube plate 3. A number of heat transfer tubes 7 having several bend radii form a heat transfer tube bundle, and the heat transfer tube bundle is surrounded by an inner cylinder 4 and is supported horizontally by a number of tube support plates 5.

A number of through-holes for allowing the heat transfer tube 7 to pass through are formed in the tube support plates 5. The tube support plates 5 are used for preventing vibration of the heat transfer tubes 7 and for maintaining the mutual spacing between the heat transfer tubes 7. In other words, since a number of heat transfer tubes 7 pass through the tube support plate 5, the mutual spacing between the heat transfer tubes 7 can be maintained, thus preventing vibration of the heat transfer tubes 7, and, furthermore, even when a lateral load (a load exerted in the horizontal direction) is exerted due to an earthquake etc., this lateral load is borne by the tube support plate 5.

In the steam generator having such a configuration, high-temperature heating fluid 6 flows into a first water chamber 8, and this heating fluid 6 flows through the heat transfer tubes 7, provides heat to be cooled, and then, flows out from a second water chamber 9. The heating fluid 6 is, for example, a nuclear reactor coolant. In addition, feedwater 31 that has entered by flowing through a feedwater nozzle 30 flows down through the space between the inner cylinder 4 and the outer cylinder 2, turns above the tube plate 3, and flows upwards along the heat transfer tubes 7. While flowing upwards, the feedwater 31 absorbs heat from the heating fluid 6 through heat exchange, is heated, is boiled, and becomes steam. This steam 33 flows out from a steam nozzle 34 and is directed to, for example, a steam turbine.

Figure 10:
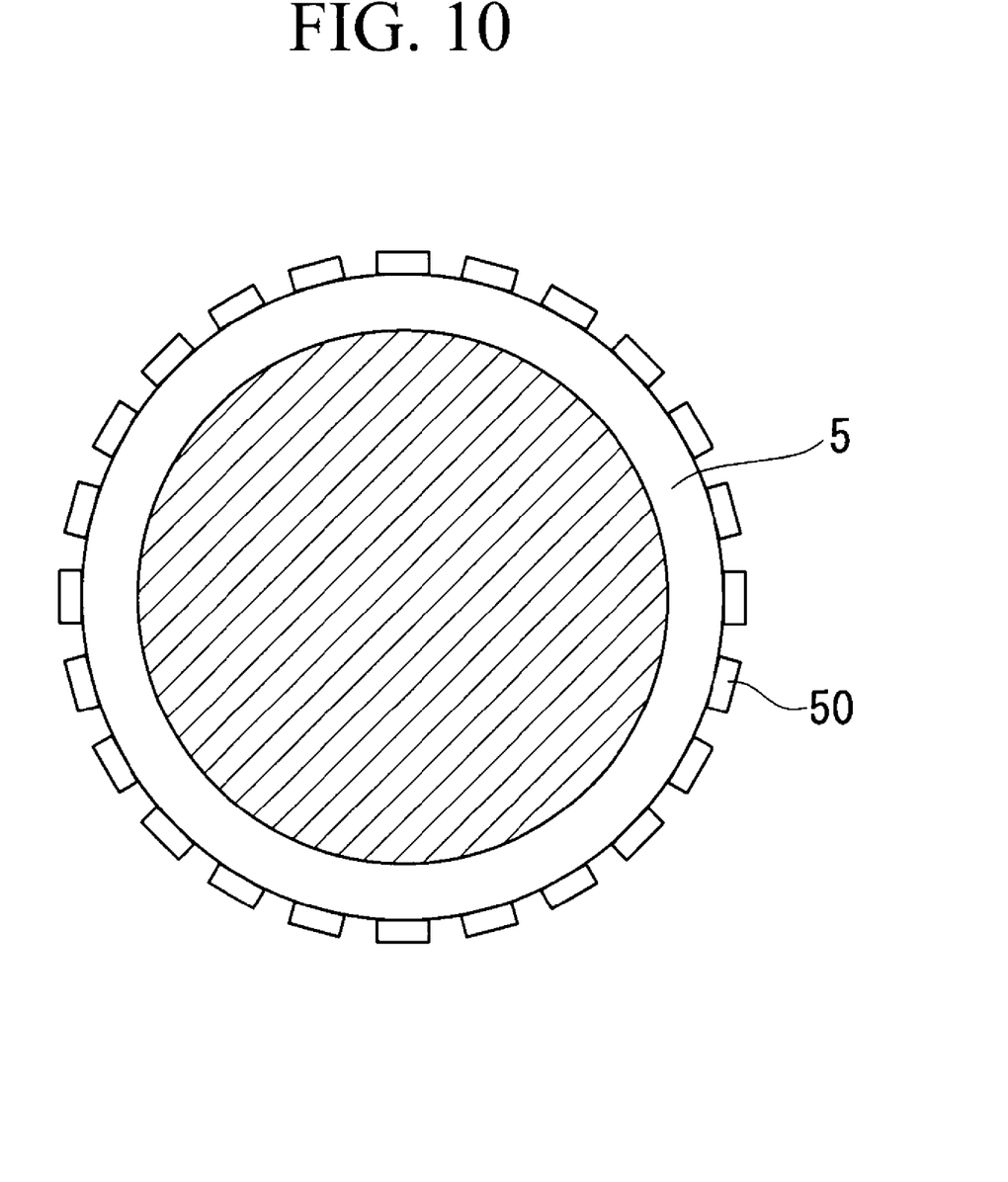
FIG. 10 is a plan view of a tube support plate taken from above the steam generator.

FIG. 10 is a plan view of the tube support plate 5 taken from above the steam generator 1. As shown in FIG. 10, wedges 50 are provided on the outer periphery of the tube support plate 5 at prescribed intervals. When the tube support plate 5 is arranged in the steam generator, these wedges 50 fill the gap between the inner cylinder 4 and the tube support plate 5.

Figure 11:
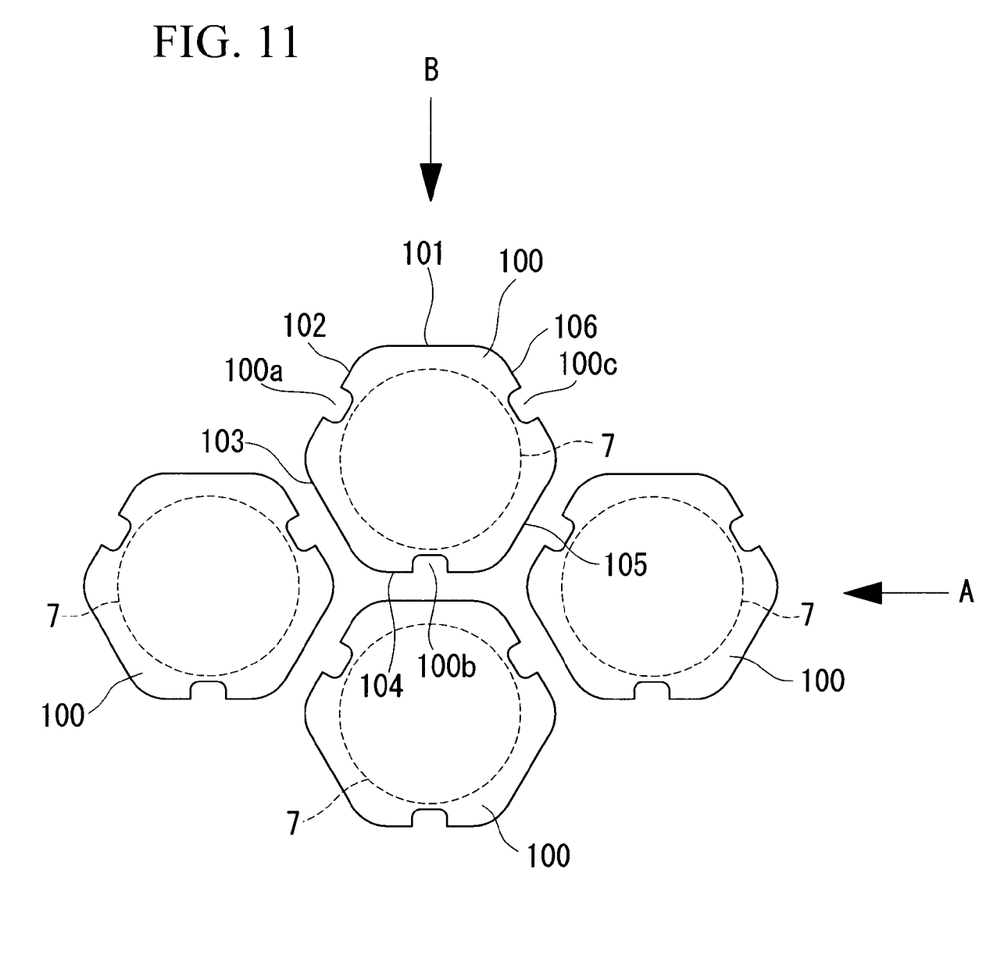
FIG. 11 is an example diagram showing the shape and arrangement of through-holes.

In addition, a number of (for example, a few thousand) through-holes 100 (see FIG. 11) for allowing the heat transfer tubes 7 to pass through are formed in the central portion (cross-hatched portion in the figure) of the tube support plate 5. As shown in FIG. 11, the through-holes 100 have, for example, a hexagonal shape, and protrusions 100a, 100b, and 100c that protrude towards the center of the through hole 100 are respectively formed on, among the six sides 101, 102, 103, 104, 105, and 106 that form the hexagonal shape, the alternate sides 102, 104, and 106. In FIG. 11, although only four through-holes 100 are illustrated, in practice, such through-holes 100 are arranged on the tube support plate 5 so as to be aligned vertically and horizontally in a grid pattern. In a state where the heat transfer tubes 7 pass through such through-holes 100, respectively, a gap is provided between the outer peripheral surface of the heat transfer tubes 7 and the inner peripheral surface of the through-holes 100, and this gap provides a flow path for the secondary cooling water and the steam. The through-holes 100 have, in addition to a function of supporting the heat transfer tubes 7, a flowpath function for allowing the secondary cooling water and the steam that flow upwards in the inner cylinder 4 to flow therethrough.

When the steam generator 1 experiences a large lateral load due to an earthquake etc., the lateral load is also propagated to the tube support plate 5. At this time, if the in-plane compressive strength of the tube support plate 5 is not sufficient, there is a risk in that the through-holes 100 will be crushed to contact with the heat transfer tubes 7, and the heat transfer tubes 7 will be deformed (damaged). In order to prevent the occurrence of such a situation, the tube support plate 5 is required to have a certain in-plane compressive strength.

Conventionally, an evaluation of the in-plane compressive strength of such a tube support plate 5 is performed by forming a small-scale test piece having the same structure as the tube support plate 5, gradually applying a lateral load to this test piece, and reading out the value of the lateral load (hereinafter referred to as "stick load") at which the through hole 100 that is formed in the tube support plate 5 is crushed and makes contact with the heat transfer tubes 7. The reason for performing the evaluation using a test piece in this way is that, since the actual dimension of the tube support plate 5 is at least 3 m in diameter and can be as large as about 6 m in diameter, test facilities, test conditions, and so forth are restricted in several ways, and it is difficult to perform the in-plane compressive strength evaluation with the actual plate.

By performing the evaluation of the in-plane compressive strength using a test piece in this way, it is possible to estimate, when a lateral load is exerted on the actual plate, how the tube support plate 5 will deform and the position in the tube support plate where the most severe damage will be caused.

CITATION LIST

Patent Literature

{PTL 1} Japanese Unexamined Patent Application, Publication No. 2008-209063

SUMMARY OF INVENTION

Technical Problem

Since the through-holes 100 are arranged as shown in FIG. 11, the in-plane strength will differ, for example, between the case where the load is exerted in the direction of arrow A in the figure and the case where the load is exerted in the direction of arrow B in the figure. In other words, the tube support plate 5 has anisotropy in that the in-plane strength varies depending on the direction of the load exerted. Therefore, there is a problem in that, if the in-plane strength evaluation is to be performed by considering the anisotropy, it is necessary to provide at least two test pieces, that is, a test piece for exerting the load in the direction of the arrow A and a test piece for exerting the load in the direction of the arrow B, and enormous cost and effort are required for producing the test pieces.

In addition, errors occur unavoidably upon production of the test pieces, and it is almost impossible to produce the test piece within the set tolerances from the viewpoint of production costs. Therefore, there is a problem in that tolerance evaluation cannot be performed.

Furthermore, as described above, although the evaluation is performed on test pieces because the evaluation of the actual plate is not possible, there is a problem in that, when evaluation results of the test pieces are applied to the actual plate, and evaluation results of the in-plane compressive strength of the actual plate are to be estimated, there is little information that supports the estimated evaluation results and confidence in the results is low.

The present invention has been conceived in light of the above-described situation, and an object thereof is to provide an in-plane compressive strength evaluation device that is capable of achieving reduction of cost and improvement of evaluation accuracy, as well as a method therefor.

Solution to Problem

In order to solve the above-described problems, the present invention employs the following solutions.

A first aspect of the present invention is an in-plane compressive strength evaluation device that is disposed in a steam generator and evaluates an in-plane compressive strength of a tube support plate, in which a number of through-holes, through which heat transfer tubes pass, are formed, the evaluation device including a memory unit in which, when a test piece having substantially a same structure as the tube support plate that is actually used is formed and an in-plane compressive strength evaluation is performed by exerting a load in a state where the heat transfer tubes having a prescribed length are inserted into the through-holes formed in the test piece, respectively, an evaluation result related to the load and a displacement of the test piece is stored as first information; a first analysis unit that obtains, by producing a structural model of the test piece and by performing a simulation of the in-plane compressive strength evaluation under same conditions as the in-plane compressive strength evaluation, second information that is an evaluation result related to the load and the displacement in the structural model; an adjustment unit that adjusts an elemental factor of the structural model that influences the in-plane compressive strength such that the second information that is obtained by the first analysis unit approaches the first information that is stored in the memory unit; and a second analysis unit that, in a state where the elemental factor that is used when the second information approaches the first information most closely, or when a difference between the second information and the first information falls within an allowable range is maintained, expands the structural model into a structural form of the tube support plate that is actually applied to the steam generator and performs the in-plane compressive strength evaluation using the expanded structural model.

According to the above-described first aspect, the in-plane compressive strength evaluation is actually performed by forming a test piece having substantially the same structure as the tube support plate that is actually used, and by exerting a load in a state where the heat transfer tubes having the prescribed length are inserted into the through-holes that are formed in this test piece, respectively. Thus, an evaluation result related to the load and the displacement in the test piece obtained at this time is stored in the memory unit as the first information.

In addition, the structural model of the test piece is produced by the first analysis unit, and the simulation of the in-plane compressive strength evaluation using this structural model of the test piece is performed under the same conditions as the actual conditions, thereby obtaining the second information, which is the evaluation result related to the load and the displacement in the structural model. When the first information and the second information are obtained, the elemental factor of the structural model is adjusted by the adjustment unit such that the second information approaches the first information. The elemental factor that is adjusted at this time is the elemental factor that influences the in-plane compressive strength. Thereafter, the structural model is produced at the actual plate level by the second analysis unit by expanding the structural model of the test piece while taking over the elemental factor that is used when the second information approaches the first information most closely, and the in-plane compressive strength evaluation is performed by using this structural model.

In this way, the elemental factor of the structural model of the test piece is adjusted such that the simulation result that is close to the evaluation result of the actual in-plane compressive strength evaluation that is performed using the test piece is obtained, and the simulation of the in-plane compressive strength evaluation is performed by expanding the structural model having the elemental factor that has provided the evaluation result closest to the actual evaluation result into the actual plate. By doing so, it is possible to perform the simulation of the actual plate using the structural model, which ensures reproducibility of the experimental result and an increase in the reliability of the evaluation result with the actual plate.

In addition, although at least two test pieces are required to be prepared conventionally in order to consider anisotropy, in the present invention, only one test piece is required since the test piece is only required for understanding the property of the in-plane compressive strength evaluation of the actual tube support plate. Therefore, it is possible to reduce the cost and effort required for forming the test piece. Furthermore, a load can be exerted under various conditions (angles, magnitudes, and so forth) in the simulation, and various evaluations can be performed.

The elemental factors of the structural model that influence the above-mentioned in-plane compressive strength include, for example, material factors of the structural model and a deformable element factor that defines a deformation of the structural model. The material factors include, for example, a material hardening rule etc. In addition, the deformable element factor is a factor that is used to simply evaluate a three-dimensional model (x, y, and z) as a two-dimensional model (x and y), and it includes, for example, a plane stress factor, a plane strain factor, and so forth. The plane stress factor is a factor that defines that the stress in the z-axis direction is zero, in other words, that the structural model deforms freely in the z-axis direction. The plane strain factor is a factor that defines that the strain in the z-axis direction is zero, in other words, that the structural model does not deform in the z-axis direction. For example, the plane stress factor is applied in a case where the thickness in the z-axis direction is small, and the plane strain factor is applied in a case where the thickness in the z-axis direction is sufficiently large.

In the above-mentioned in-plane compressive strength evaluation device, the second analysis unit may perform the in-plane compressive strength evaluation by exerting a sinusoidally or a cosinusoidally distributed load to wedges that are disposed on an outer periphery of the tube support plate at prescribed intervals.

In this way, by exerting a sinusoidally or a cosinusoidally distributed load on the outer periphery of the tube support plate, it is possible to perform the simulation of the load that would be exerted on the tube support plate when vibration is propagated to the tube support plate due to an earthquake etc., and to exert a more realistic load on the tube support plate. Therefore, the behavior etc. of the tube support plate and the internal parts thereof in the event of an actual earthquake etc. can be understood.

A second aspect of the present invention is an in-plane compressive strength evaluation method that evaluates an in-plane compressive strength of a tube support plate that is disposed in a steam generator and in which are formed a number of through-holes through which heat transfer tubes pass, the method including a process of forming a test piece having substantially a same structure as the tube support plate that is actually used, performing an in-plane compressive strength evaluation by exerting a load in a state where the heat transfer tubes having a prescribed length are inserted into the through-holes formed in the test piece, respectively, and obtaining an evaluation result related to the load and a displacement in the test piece as first information; a process of obtaining second information that is an evaluation result related to the load and the displacement in a structural model by producing the structural model of the test piece, and by performing a simulation of the in-plane compressive strength evaluation under same conditions as the in-plane compressive strength evaluation; a process of adjusting an elemental factor of the structural model that influences the in-plane compressive strength such that the second information approaches the first information; and a process of, in a state where the elemental factor that is used when the second information approaches the first information most closely, or when a difference between the second information and the first information falls within an allowable range is maintained, expanding the structural model into a structural form of the tube support plate that is actually applied to the steam generator and performing the in-plane compressive strength evaluation using the expanded structural model.

Advantageous Effects of Invention

The present invention affords an advantage in that cost reduction can be achieved and evaluation accuracy can be improved.

DESCRIPTION OF EMBODIMENTS

An embodiment of an in-plane compressive strength evaluation device and a method therefor according to the present invention will be described below with reference to the drawings.

An in-plane compressive strength evaluation device according to one embodiment of the present invention is a device that evaluates the in-plane compressive strength of a tube support plate that is disposed in a steam generator, which is used in a nuclear power plant, and that has a number of through-holes through which heat transfer tubes pass through. The configuration of the steam generator and the configuration of the tube support plate, which is an evaluation object of the in-plane compressive strength evaluation device according to this embodiment, are shown in FIGS. 9 and 10, and the explanations thereof are described as above. In other words, as shown in FIGS. 10 and 11, a number of through-holes 100 for allowing the heat transfer tubes 7 to pass through are formed in the central portion of the tube support plate 5. The tube support plate is disposed horizontally in the steam generator 1 shown in FIG. 9, and the heat transfer tubes 7 pass through the through-holes 100 perpendicularly. As shown in FIG. 11, the through-holes 100 have, for example, a hexagonal shape. In addition, in a state where the heat transfer tubes 7 pass through the through-holes 100, a gap is formed between the outer peripheral surface of the heat transfer tubes 7 and the inner peripheral surface of the through-holes 100, and this gap serves as a flow path for the secondary cooling water and the steam.

Figure 1:
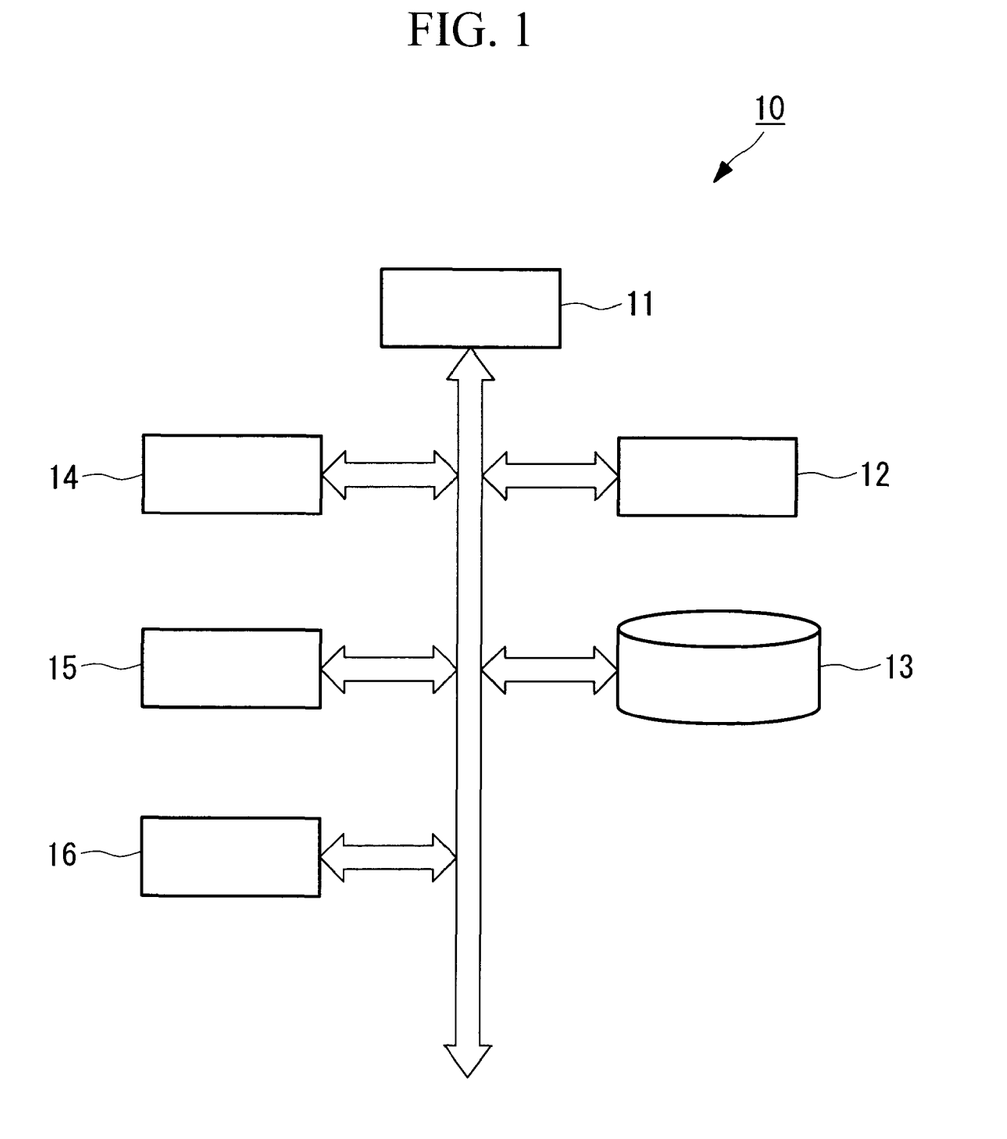
FIG. 1 is a block diagram showing, in outline, the configuration of an in-plane compressive strength evaluation device according to one embodiment of the present invention.

FIG. 1 shows, in outline, the configuration of an in-plane compressive strength evaluation device according to this embodiment. As shown in FIG. 1, an in-plane compressive strength evaluation device 10 according to this embodiment is a computer system (data processing system) that is provided with a CPU (central processing unit) 11, a main storage device 12 such as RAM (random access memory), an auxiliary memory device 13, an input device 14 such as a keyboard or a mouse, a display device 15, and a communication device 16 that communicates with external devices to transfer information.

The auxiliary memory device 13 is a computer-readable recording medium, for example, a magnetic disk, a magneto-optical disk, a CD-ROM, a DVD-ROM, a semiconductor memory, and so forth. Several programs (for example, an in-plane compressive strength evaluation program) are stored in this auxiliary memory device 13, and the CPU 11 reads out the program from the auxiliary memory device 13 to the main storage device 12 and executes the program to realize various processes.

Figure 2:
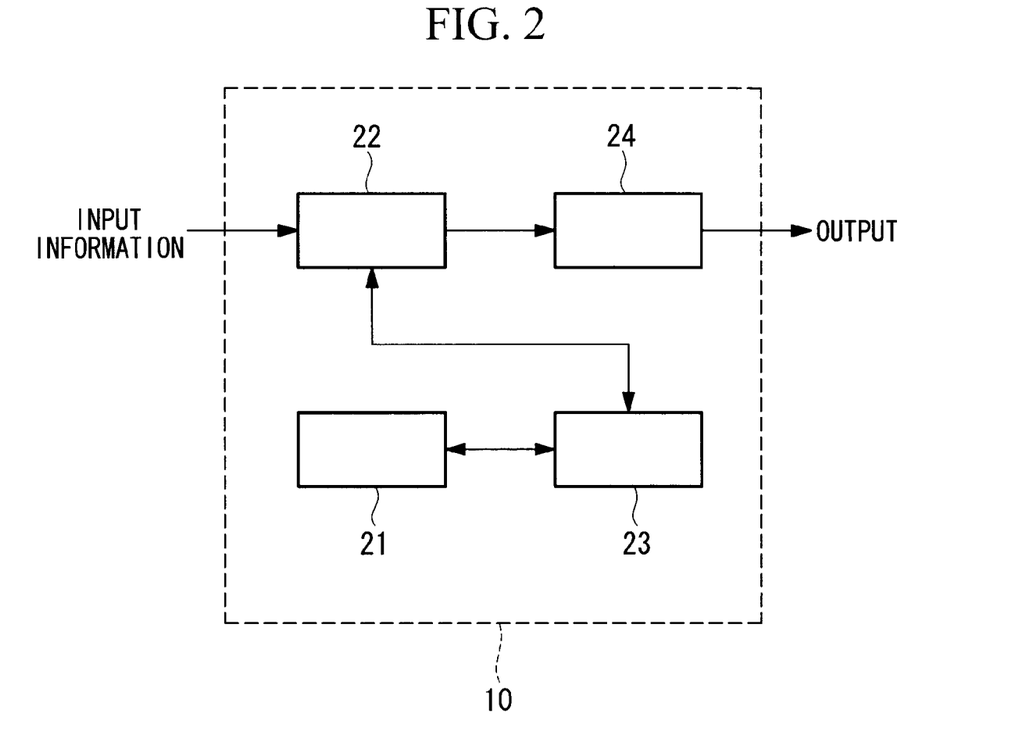
FIG. 2 is a functional block diagram showing, in an expanded manner, functions of an in-plane compressive strength evaluation device according to one embodiment of the present invention.

FIG. 2 is a functional block diagram showing, in an expanded manner, functions of the in-plane compressive strength evaluation device 10. As shown in FIG. 2, the in-plane compressive strength evaluation device 10 is provided with a memory unit 21, a first analysis unit 22, an adjustment unit 23, and a second analysis unit 24.

A test piece having substantially the same structure as the tube support plate 5 which is actually used in the steam generator is formed, and the heat transfer tubes 7 having prescribed lengths are inserted into the through-holes 100 formed in the test piece, respectively. In this state, a load is exerted to perform the in-plane compressive strength evaluation. An evaluation result related to the load and the displacement in the test piece at this time is stored in the memory unit 21 as first information.

The in-plane compressive strength evaluation is performed as described below, for example.

Figure 3:
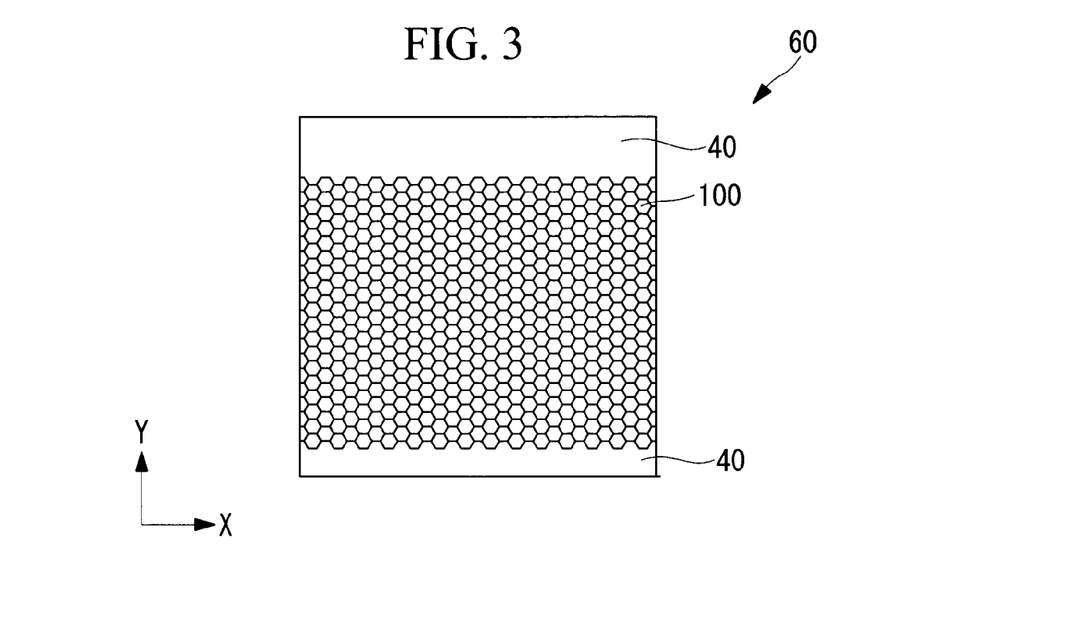
FIG. 3 is a diagram showing, in outline, the configuration of a test piece.

In the in-plane compressive strength evaluation performed prior to the simulation, a test piece having substantially the same structure as the tube support plate 5 which is actually used in the steam generator 1 is formed. FIG. 3 shows, in outline, a configuration of the test piece. As shown in FIG. 3, the test piece 60 has a square shape and has a configuration in which a number of through-holes 100 are arranged between outer frame portions 40. The outer frame portions 40 are provided only on two opposing sides (two sides along the X-direction in FIG. 3) of the four sides.

Figure 4:
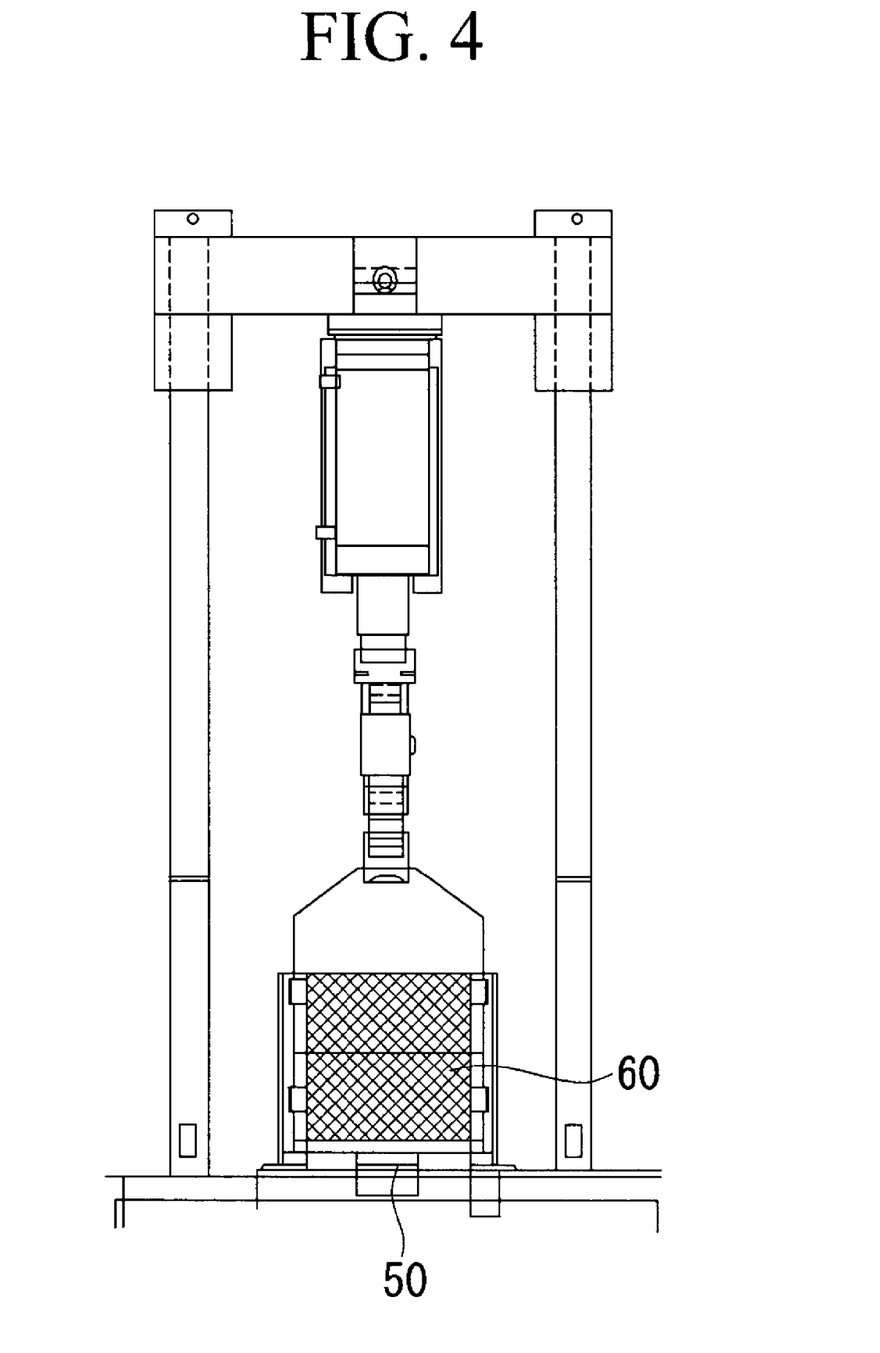
FIG. 4 is a diagram showing, in outline, the configuration of a loading jig that is used in an in-plane compressive strength evaluation.
Figure 5:
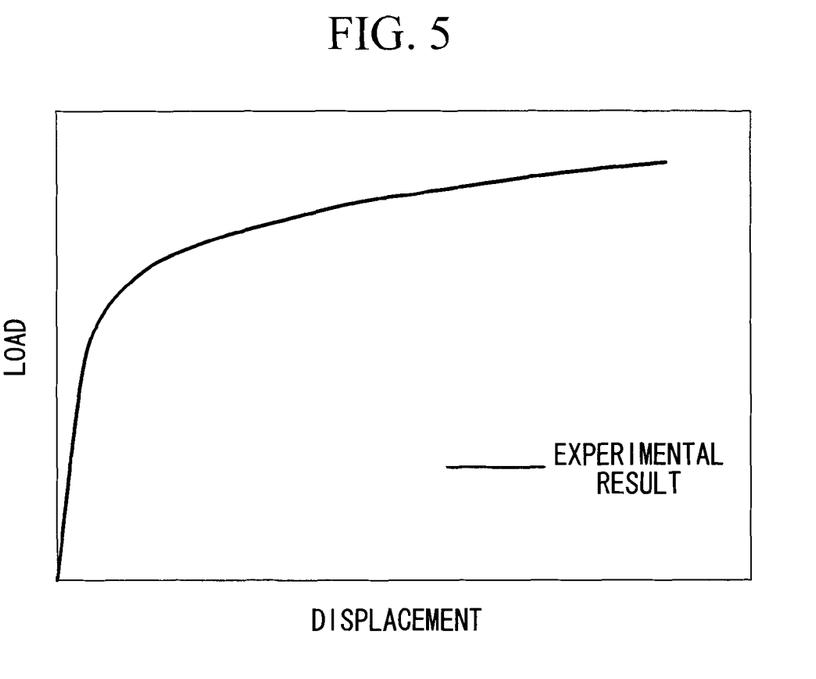
FIG. 5 is an example diagram showing evaluation results of an in-plane compressive strength evaluation.

FIG. 4 is a diagram showing, in outline, the configuration of a loading jig that is used in the in-plane compressive strength evaluation. The wedges 50 are disposed at the base of the loading jig, and the test piece 60 is fixed above these wedges 50. At this time, the test piece 60 is fixed to the loading jig such that the outer frame portions 40 are positioned at the bottom and the top, in other words, such that, in FIG. 3, the X-direction becomes the horizontal direction and Y-axis extends in the vertical direction. In this state, the heat transfer tubes 7 having the prescribed length are inserted into the respective through-holes 100 in the test piece 60. In a state where the heat transfer tubes 7 are inserted into the respective through-holes 100 in the test piece 60, a load is exerted on the test piece 60 from the upper surface portion thereof, thereby performing the in-plane compressive strength evaluation. The in-plane compressive strength evaluation is performed by exerting the load in the prescribed unit and by reading out the vertical displacement of the test piece 60 at this time on two displacement gauges (not shown) disposed on both sides of the test piece 60. FIG. 5 shows an example of the evaluation result of the in-plane compressive strength evaluation. In FIG. 5, the horizontal axis indicates the displacement and the vertical axis indicates the load. In the region where the load is small, the change in the displacement is small due to elastic deformation; however, when the load exceeds a certain value, the displacement per prescribed amount of load becomes larger as the elastic deformation is replaced by plastic deformation.

In addition, in the in-plane compressive strength evaluation, a detection of the stick load is performed as well as acquisition of the graph shown in FIG. 5. This stick load is the value of the load obtained when a load is exerted on the tube support plate 5 from the outer periphery thereof to cause a gradual deformation of the through-holes 100 that are formed in the plate, and the inner peripheral surface of any one of the through-holes 100 is caused to make contact with the outer peripheral surface of the heat transfer tubes 7 that pass through the through-holes 100. This stick load is detected by, for example, an examiner checking the state of all the through-holes 100 every time the load is exerted in the prescribed unit, and by reading out the value of the load being exerted when at least one through hole in which the inner peripheral surface of the through-holes 100 is in contact with the outer peripheral surface of the heat transfer tubes 7 is found.

When the information (hereinafter referred to as "first information") in which the load and the displacement are associated, as shown in FIG. 5, and the stick load are obtained by performing the in-plane compressive strength evaluation, this first information and stick load are stored in the memory unit of the in-plane compressive strength evaluation device (see FIG. 2).

In this embodiment, although a configuration in which the loading jig having a configuration shown in FIG. 4 is used, the load is exerted on the test piece 60 from the upper surface portion thereof, and this load is received by the wedges 50 disposed on the base is employed, the configuration of the loading jig used in the in-plane compressive strength evaluation is not limited thereto, and a jig that is capable of performing a test in which a load is exerted on the test piece 60 and a relationship between the load and the displacement is obtained is adequate.

Referring back to FIG. 2, by producing a structural model of the test piece 60 used in the above-described actual in-plane compressive strength evaluation and by performing a simulation of the in-plane compressive strength evaluation under the same conditions as the actual in-plane compressive strength evaluation, the first analysis unit 22 obtains second information in which the load and the displacement in the structural model are associated.

Specifically, the first analysis unit 22 has a program that produces the structural model of the test piece used in the above-described actual in-plane compressive strength evaluation on the basis of the information input from the input device 14 (see FIG. 1) and produces the structural model of the test piece by executing this program.

The information input from the input device 14 includes, for example, a form factor, a material factor, a boundary condition, a deformable element factor, and so forth. The form factor includes, for example, the size of the entire model, the shape and arrangement of the through-holes, and so forth. The material factor includes, for example, the Young's modulus, a material hardening rule, and so forth. The boundary condition includes, for example, positions of the wedges 50, constraining conditions of the edges of the test piece 60, and so forth. In addition, the deformable element factor is the deformable element factor that defines the deformation of the structural model and is a factor that is used for simply evaluating a three-dimensional model (x, y, and z) as a two-dimensional model (x and y). Specifically, the deformable element factor includes a plane stress factor, a plane strain factor, and so forth. The plane stress factor is a factor that defines the stress in the z-axis direction to be zero, in other words, that the structural model deforms freely in the z-axis direction. The plane strain factor is a factor that defines the strain in the z-axis direction to be zero, in other words, that the structural model does not deform in the z-axis direction. For example, the plane stress factor is applied in a case where the thickness in the z-axis direction is small, and the plane strain factor is applied in a case where the thickness in the z-axis direction is sufficiently large.

The above-mentioned information is input by an operator via the input device 14, and the first analysis unit 22 produces the structural model on the basis of the information. Then, the first analysis unit 22 performs the simulation of the in-plane compressive strength evaluation under the same conditions as the actual in-plane compressive strength evaluation by using a numerical analysis method. By doing so, the second information in which the load and the displacement in the structural model are associated is obtained. An example of the numerical analysis method includes the finite element method.

The adjustment unit 23 adjusts the elemental factors that influence the in-plane compressive strength in the structural model such that the second information obtained by the first analysis unit 22 approaches the first information stored in the memory unit 21.

Specifically, the adjustment unit 23 first calculates a difference between the first information stored in the memory unit 21 and the second information obtained by the first analysis unit 22 and determines whether or not the maximum value of this difference falls within the pre-set allowable range.

As a result of this, if the maximum value of the difference does not fall within the allowable range, at least one of the material factor and the deformable element factor of the above-mentioned several elemental factors that are used to produce the structural model is changed to modify the structural model. Specifically, in this embodiment, the material hardening rule is adjusted as the material factor. In addition, any factor of a plurality of deformable element factors, such as the pre-set plane stress factor, plane strain factor, and so forth, is selected as the deformable element factor, for example.

The first analysis unit 22 then performs the in-plane compressive strength evaluation again using the modified structural model to obtain the second information that differs from the last time. Thereafter, the adjustment unit 23 compares this second information with the first information once again, and determines whether or not the maximum value of the difference falls within the allowable range. The adjustment unit 23 repeatedly updates the combination of the material hardening rule of the material factor and the deformable element factor until the maximum value of the difference falls within the allowable range and obtains the conditions of the factors with which the maximum value of the difference falls within the allowable range.

The second analysis unit 24 expands the structural model, having the material factors that have been adjusted by the adjustment unit 23 such that the difference between the second information and the first information falls within the allowable range, into the structural form of the tube support plate 5 that is applied to the actual steam generator 1 and performs the in-plane compressive strength evaluation using the expanded structural model. Specifically, upon the expansion into the actual plate, the several information related to the actual plate are input through the input device 14. The information that is input here includes, for example, the form factor and the boundary conditions. The second analysis unit 24 produces the structural model for the actual plate by updating the form factor and the boundary conditions, of the several input information that are used by the first analysis unit 22 for producing the structural model, with the input information that is input at this time.

The material factor is inherited without any modification when the structural model of the test piece used in the first analysis unit 22 is expanded into the actual plate. In this way, by producing the structural model of the actual plate by employing the values of the material factor for the test piece without any modification, the structural model of the actual plate can be produced in such a manner that a property that strongly influences the evaluation of the in-plane compressive strength is inherited without any modification. Therefore, the evaluation result of the in-plane compressive strength evaluation of the actual plate that is performed using this structural model is highly reliable.

Figure 6:
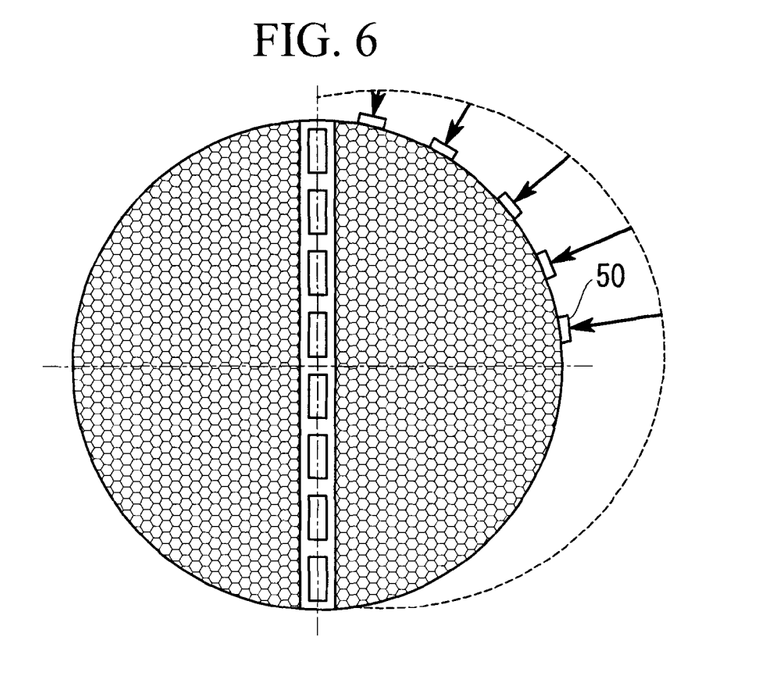
FIG. 6 is an example diagram showing a load exerted on a wedge in a simulation of an in-plane compressive strength evaluation of an actual plate.

As shown in FIG. 6, the simulation of the in-plane compressive strength evaluation with the structural model of the actual plate is performed by exerting a sinusoidal (or cosinusoidal) load on the respective wedges 50. By obtaining the load and the displacement when such a load is exerted, the in-plane compressive strength evaluation is performed. In addition, the stick load may also be detected in the simulation of the in-plane compressive strength evaluation of the actual plate.

Figure 7:
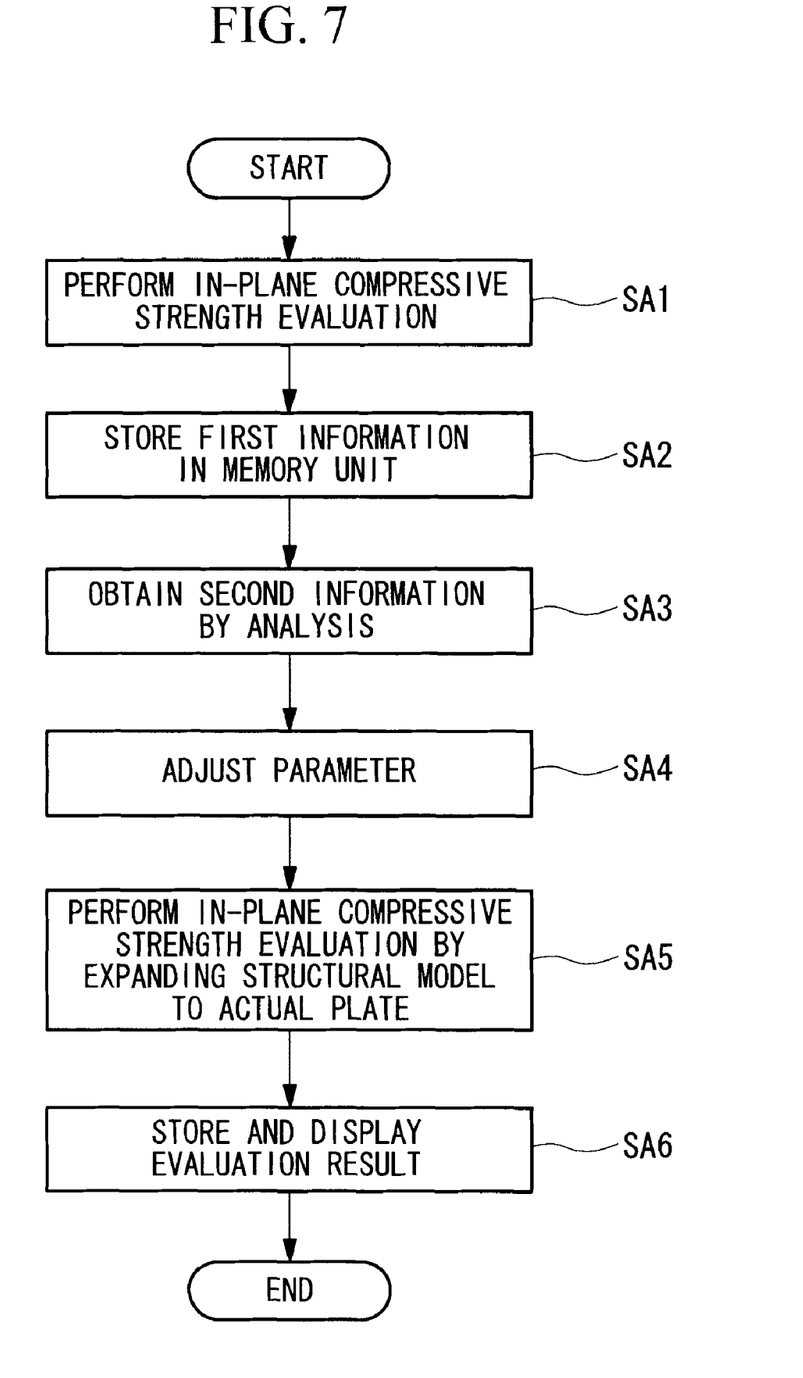
FIG. 7 is a flowchart showing operations of an in-plane compressive strength evaluation device according to one embodiment of the present invention.

Next, the operation of the in-plane compressive strength evaluation device 10 having the above-mentioned configuration will be briefly described with reference to FIG. 7.

Prior to the in-plane compressive strength evaluation with the in-plane compressive strength evaluation device 10, an actual in-plane compressive strength evaluation using the test piece 60 is performed (Step SA1), and the first information that associates the load and the displacement in the test piece, which are obtained at this time, is stored in the memory unit 21 (Step SA2).

In the in-plane compressive strength evaluation with the in-plane compressive strength evaluation device 10, the structural model of the test piece 60 is produced by the first analysis unit 22, this structural model of the test piece 60 is used to perform the simulation of the in-plane compressive strength evaluation under the same conditions as the actual conditions, and the second information that associates the load and the displacement in the structural model is obtained (Step SA3).

After obtaining the first information and the second information, the adjustment unit 23 adjusts the material factor of the structural model such that the second information approaches the first information and selects the deformable element factor (Step SA4). The second analysis unit 24 then expands the structural model that has the material factor that provides the second information that is closest to the first information into the structural form of the tube support plate that is actually applied to the steam generator and performs the in-plane compressive strength evaluation using the expanded structural model (Step SA5). The in-plane compressive strength evaluation result obtained with the structural model of the actual plate is stored in the memory unit 21 and is displayed on the display device 15 by being processed into a graph, thereby being presented to the operator (Step SA6).

As described above, according to the in-plane compressive strength evaluation device and the method therefor of this embodiment, the parameters of the structural model are calibrated such that the simulation result is close to the evaluation result of the actually performed in-plane compressive strength evaluation, and the simulation of the in-plane compressive strength evaluation is performed by expanding the structural model having the elemental factors that have provided the evaluation result closest to the actual evaluation result into the actual plate. By doing so, it is possible to perform the simulation of the actual plate using the structural model, which ensures reproducibility of the experimental result and an increase in the reliability of the evaluation result with the actual plate.

Furthermore, if a structural model having the same property as the test piece can be produced, the direction in which the load is exerted can be set freely when performing the simulation. Therefore, although two test pieces are required to be prepared conventionally in order to consider the anisotropy, in this embodiment, only one test piece is required, and so, it is possible to reduce the cost and time needed for producing the test piece.

Figure 8:
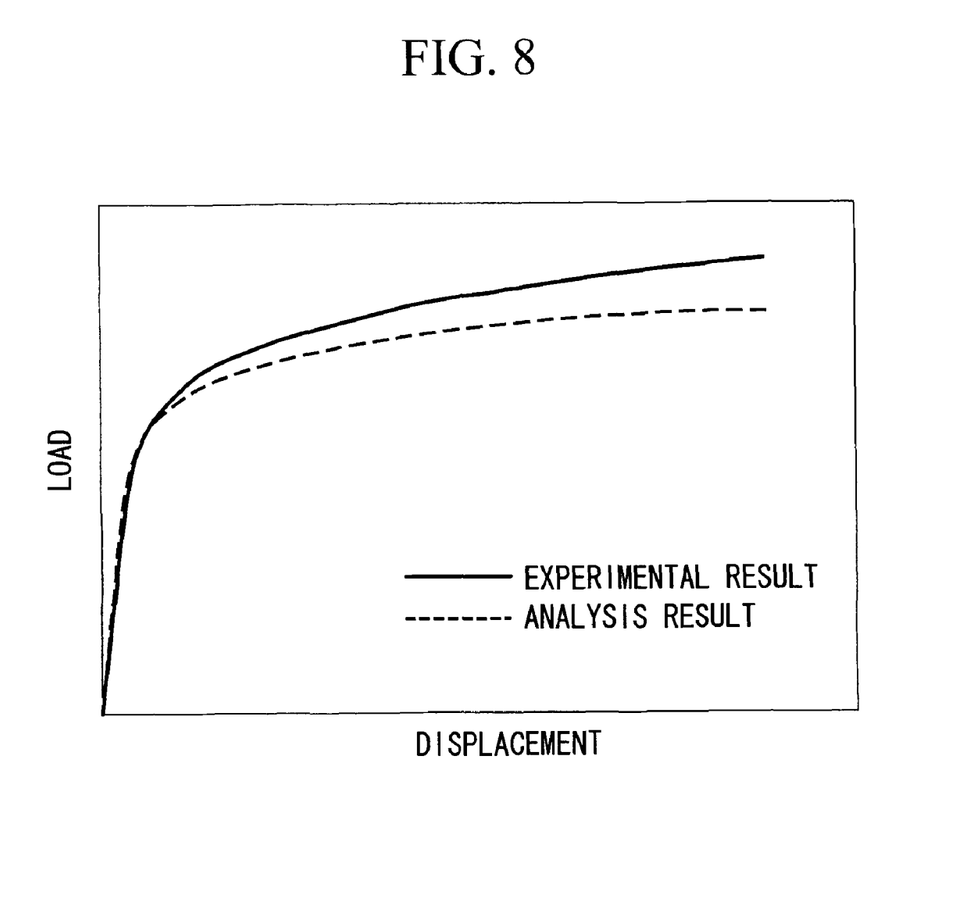
FIG. 8 is a diagram showing a comparison between evaluation results of an in-plane compressive strength evaluation of an actual test piece and evaluation results of an in-plane compressive strength evaluation by simulation.

In this embodiment, although the descriptions assumed that the adjustment unit 23 automatically updates the material hardening rule of the material factor and the deformable element factor to obtain the suitable values, an operator, for example, may re-input values of the material factor and the deformable element factor through the input device 14 to achieve the adjustment of the material factor and the deformable element factor. In this case, for example, it is possible to consider an aspect in which the material factor is adjusted by displaying a graph, such as that shown in FIG. 8, in which the first information and the second information are shown in comparison, on the display device 15, and by an operator manually inputting a new value of the material factor through the input device 14 while checking this display screen.

In addition, in this embodiment, although the descriptions assumed that the adjustment of the elemental factor of the structural model is finished when the maximum value of the difference between the first information and the second information falls within the allowable range, and the structural model of the test piece having the elemental factor at this time is expanded into the actual plate, instead of this, for example, the adjustment of the elemental factor for the structural model may be finished when the maximum value of the difference between the first information and the second information becomes smallest.

In addition, in this embodiment, the properties as shown in FIG. 5, in which the load and the displacement are associated, are employed as the first information and the second information, and the adjustment of the elemental factor for the structural model is finished when the maximum value of the difference between these properties falls within the allowable range; however, the stick loads may be employed as the first information and the second information. In this case, the adjustment unit 23 may finish the adjustment of the elemental factor for the structural model when, for example, the difference between the stick load obtained in the actual in-plane compressive strength evaluation and the stick load obtained in the first analysis unit 22 becomes the smallest, or when the difference between the stick loads falls within a preset allowable range (for example, within 5%).

REFERENCE SIGNS LIST 1 steam generator
5 tube support plate
7 heat transfer tube
10 in-plane compressive strength evaluation device
11 CPU
12 main storage device
13 auxiliary memory device
14 input device
15 display device
16 communication device
21 memory unit
22 first analysis unit
23 adjustment unit
24 second analysis unit
40 outer frame portion
50 wedge
60 test piece
100 through-hole

The invention claimed is:

1. An in-plane compressive strength evaluation device that is disposed in a steam generator and evaluates an in-plane compressive strength of a tube support plate, in which are formed a number of through-holes through which heat transfer tubes pass, the in-plane compressive strength evaluation device comprising:
a memory unit in which, when a test piece having substantially a same structure as the tube support plate that is actually used is formed and an in-plane compressive strength evaluation is performed by exerting a load in a state where the heat transfer tubes having a prescribed length are inserted into the through-holes formed in the test piece, respectively, an evaluation result related to the load and a displacement of the test piece is stored as first information;
a first analysis unit that obtains, by producing a structural model of the test piece and by performing a simulation of the in-plane compressive strength evaluation under same conditions as the in-plane compressive strength evaluation, second information that is an evaluation result related to the load and the displacement in the structural model;
an adjustment unit that adjusts an elemental factor of the structural model that influences the in-plane compressive strength such that the second information that is obtained by the first analysis unit approaches the first information that is stored in the memory unit; and
a second analysis unit that, in a state where the elemental factor that is used when the second information approaches the first information most closely, or when a difference between the second information and the first information falls within an allowable range is maintained, expands the structural model into a structural form of the tube support plate that is actually applied to the steam generator and performs the in-plane compressive strength evaluation using the expanded structural model.

2. An in-plane compressive strength evaluation device according to claim 1, wherein the second analysis unit performs the in-plane compressive strength evaluation by exerting a sinusoidally or a cosinusoidally distributed load to wedges that are disposed on an outer periphery of the tube support plate at prescribed intervals.

3. An in-plane compressive strength evaluation method that evaluates an in-plane compressive strength of a tube support plate that is disposed in a steam generator and in which are formed a number of through-holes through which heat transfer tubes pass, the in-plane compressive strength evaluation method comprising:
a process of forming a test piece having substantially a same structure as the tube support plate that is actually used, performing an in-plane compressive strength evaluation by exerting a load in a state where the heat transfer tubes having a prescribed length are inserted into the through-holes formed in the test piece, respectively, and obtaining an evaluation result related to the load and a displacement in the test piece as first information;
a process of obtaining second information that is an evaluation result related to the load and the displacement in a structural model by producing the structural model of the test piece and by performing a simulation of the in-plane compressive strength evaluation under same conditions as the in-plane compressive strength evaluation;

a process of adjusting an elemental factor of the structural model that influences the in-plane compressive strength such that the second information approaches the first information; and a process of, in a state where the elemental factor that is used when the second information approaches the first information most closely, or when a difference between the second information and the first information falls within an allowable range is maintained, expanding the structural model into a structural form of the tube support plate that is actually applied to the steam generator and performing the in-plane compressive strength evaluation using the expanded structural model.

* * * * *